United States Patent
Fukuda et al.

(10) Patent No.: US 7,227,032 B2
(45) Date of Patent: Jun. 5, 2007

(54) 3,3-DIALKOXY-2-HYDROXYIMINOPROPIO-NITRILES, PROCESS FOR PREPARATION THEREOF AND PROCESS OF PREPARING 5-AMINO-4-NITROSOPYRAZOLES OR SALTS THEREOF BY THE USE OF THE SAME

(75) Inventors: Yasuhisa Fukuda, Ube (JP); Shoji Shikita, Ube (JP); Tadashi Murakami, Ube (JP)

(73) Assignee: Ube Industries, Ltd., Ube-shi, Yamaguchi (JP)

( * ) Notice: Subject to any disclaimer, the term of this patent is extended or adjusted under 35 U.S.C. 154(b) by 465 days.

(21) Appl. No.: 10/480,576

(22) PCT Filed: Jun. 12, 2002

(86) PCT No.: PCT/JP02/05827

§ 371 (c)(1),
(2), (4) Date: Dec. 12, 2003

(87) PCT Pub. No.: WO02/100821

PCT Pub. Date: Dec. 19, 2002

(65) Prior Publication Data

US 2004/0116732 A1   Jun. 17, 2004

(30) Foreign Application Priority Data

Jun. 12, 2001 (JP) ............... 2001-176897
Sep. 6, 2001 (JP) ............... 2001-269670

(51) Int. Cl.
  *C07C 249/04* (2006.01)
(52) U.S. Cl. .................................... 558/446
(58) Field of Classification Search .............. 558/446
  See application file for complete search history.

(56) References Cited

U.S. PATENT DOCUMENTS 3,910,928 A * 10/1975 McCall et al. ............... 546/246
3,957,782 A    5/1976 Hoehn
6,452,019 B1   9/2002 Cook

FOREIGN PATENT DOCUMENTS

DE       34 32 983 A    4/1985
JP       60-56981 A     4/1985
JP       62-273979 A    11/1987

OTHER PUBLICATIONS

K.A. Ogloblin et al, Interaction of Nitrosyl Chloride With Unsaturated Compounds XXVIII. Reaction With the Nitriles of Methacrylic and Crotonic Acids, *Journal of Organic Chemistry of the USSR* (*Zhurnal Organicheskoi Khimii*), vol. 5, No. 10, pp. 1679-1682 (1969).

* cited by examiner

*Primary Examiner*—James O. Wilson
*Assistant Examiner*—Ebenezer Sackey
(74) *Attorney, Agent, or Firm*—Frishauf, Holtz, Goodman & Chick, P.C.

(57) ABSTRACT

The present invention is to provide a 3,3-dialkoxy-2-hydroxyiminopropionitrile represented by the formula (1):

$$\begin{array}{c} R^1O \quad NOH \\ \diagdown / \\ \diagup \diagdown \\ R^2O \quad CN \end{array} \quad (1)$$

wherein $R^1$ and $R^2$ may be the same or different from each other, and each represent an alkyl group having 1 to 8 carbon atoms, a process for preparing the same, and a process for preparing a 5-amino-4-nitrosopyrazole compound represented by the formula (4):

$$(4)$$

[structure showing pyrazole with NO at 4-position, NH$_2$ at 5-position, and R$^4$ on N1]

wherein $R^4$ represents a hydrogen atom, an alkyl group which may have a substituent(s) or an aryl group which may have a substituent(s),
or an acid salt thereof using the same.

10 Claims, No Drawings ized application of International Application PCT/JP02/05827 filed Jun. 12, 2002.

1. Technical Field

The present invention relates to a novel 3,3-dialkoxy-2-hydroxyiminopropionitrile which is useful as an intermediate starting material for medicines, agricultural chemicals and others, and a process for producing the same, and further relates to a process for producing a 5-amino-4-nitrosopyrazole compound or an acid salt which is useful as an intermediate starting material for medicines, agricultural chemicals and others using the same.

2. Background Art

The 3,3-dialkoxy-2-hydroxyiminopropionitrile of the present invention is a novel compound and a process for producing the same has never conventionally been known.

On the other hand, 5-amino-4-nitrosopyrazole compound can be utilized as a synthetic starting material of 4,5-diaminopyrazole compound, etc., which is useful as a hair dye or an intermediate for an antitumor agent (for example, Japanese Provisional Patent Publication No. Sho. 60-56981 (which corresponds to DE 3432983), Japanese Provisional Patent Publication No. Sho. 62-273979, and Japanese PCT Provisional Patent Publication No. Hei. 7-502542 (which corresponds to U.S. Pat. No. 5,663,366)).

In the prior art, as a preparation method of 5-amino-4-nitrosopyrazole compound or an acid salt thereof, for example, in Japanese Provisional Patent Publication No. Sho. 62-273979, there is disclosed a method of obtaining 5-amino-1-(2-hydroxyethyl)-4-nitrosopyrazole hydrochloride by reacting isoamyl nitrite with 5-amino-1-(2-hydroxyethyl)-pyrazole in the presence of hydrogen chloride. However, according to this method, there are problems that the pyrazole used as a starting material cannot easily be obtained and a yield of the objective material is low.

An object of the present invention is to provide a novel 3,3-dialkoxy-2-hydroxyiminopropionitrile and a process for producing the same.

Another object of the present invention is to provide a process for producing a 5-amino-4-nitrosopyrazole compound or an acid salt thereof in a high yield by a simple and easy method from starting materials easily available.

SUMMARY OF THE INVENTION

The present invention relates to a 3,3-dialkoxy-2-hydroxyiminopropionitrile represented by the following formula (1):

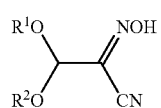
(1)

wherein $R^1$ and $R^2$ may be the same or different from each other, and represent an alkyl group having 1 to 8 carbon atoms.

The present invention also relates to a process for producing the 3,3-dialkoxy-2-hydroxyiminopropionitrile represented by the above-mentioned formula (1) which comprises reacting a 3-alkoxyacrylonitrile represented by the following formula (2):

(2)

wherein $R^3$ represents an alkyl group having 1 to 4 carbon atoms, with a nitrosyl halide in the presence of an alcohol.

The present invention further relates to a 5-amino-4-nitrosopyrazole compound represented by the following formula (4):

(4)

wherein $R^4$ represents a hydrogen atom, an alkyl group which may have a substituent(s) or an aryl group which may have a substituent(s), or an acid salt thereof, which comprises reacting the 3,3-dialkoxy-2-hydroxyiminopropionitrile represented by the above-mentioned formula (1) with a hydrazine compound represented by the formula (3):

$H_2NNHR^4$ (3)

wherein $R^4$ has the same meaning as defined above, in the presence of an acid.

The present invention further relates to a process for producing the 5-amino-4-nitrosopyrazole compound represented by the above-mentioned formula (4) which comprises reacting the 3-alkoxyacrylonitrile represented by the above-mentioned formula (2) with a nitrosyl halide in the presence of an alcohol, and then, further reacting the hydrazine compound represented by the above-mentioned formula (3) in the presence of an acid.

BEST MODE FOR CARRYING OUT THE INVENTION

The 3,3-dialkoxy-2-hydroxyiminopropionitrile according to the present invention is shown by the above-mentioned formula (1).

In the formula (1), $R^1$ and $R^2$ may be the same or different from each other, and represent an alkyl group having 1 to 8 carbon atoms, specifically, there may be mentioned, for example, a methyl group, an ethyl group, a propyl group, a butyl group, a pentyl group, a hexyl group, a heptyl group and an octyl group, preferably a methyl group and a butyl group. These groups may include the respective isomers. Incidentally, 3,3-dialkoxy-2-hydroxyiminopropionitrile of the present invention has an oxime group, so that some isomers exist such as E isomer, Z isomer and the like, and any isomers are included in the present invention.

Incidentally, the above-mentioned 3,3-dialkoxy-2-hydroxyiminopropionitrile can be led to a 5-amino-1-(2-hydroxyethyl)-4-nitrosopyrazole hydrochloride represented by the following formula (5):

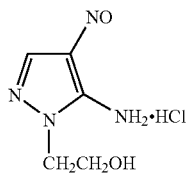

(5)

by reacting it with a 2-hydroxyethylhydrazine in the presence of hydrochloric acid (mentioned in Example 4 below), and the 5-amino-1-(2-hydroxyethyl)-4-nitrosopyrazole hydrochloride thus led can be utilized as a synthetic starting material for a pyrazolopyrazine compound which is an effective ingredient of an antitumor agent as mentioned above (for example, Japanese Provisional Patent Publications No. 60-56981, No. 62-273979, and Japanese PCT Provisional Patent Publication No. 7-502542).

The 3,3-dialkoxy-2-hydroxyiminopropionitrile of the present invention can be obtained by reacting the 3-alkoxyacrylonitrile represented by the above-mentioned formula (2) with a nitrosyl halide in the presence of an alcohol.

In the formula (2), $R^3$ represents an alkyl group having 1 to 4 carbon atoms, and, for example, it is a methyl group, an ethyl group, a propyl group or a butyl group. These groups may also include various kinds of isomers.

As an alcohol to be used in the reaction of the present invention, there may be mentioned an alcohol having an alkyl group having 1 to 8 carbon atoms (including various kinds of isomers), and there may be used, for example, methanol, ethanol, n-propyl alcohol, isopropyl alcohol, n-butyl alcohol, t-butyl alcohol, pentyl alcohol, hexyl alcohol, heptyl alcohol and octyl alcohol, preferably methanol, ethanol, n-propyl alcohol, isopropyl alcohol, n-butyl alcohol, t-butyl alcohol, more preferably methanol.

An amount of the above-mentioned alcohol is preferably 0.5 to 100 mols, more preferably 0.8 to 50 mols based on 1 mol of the 3-alkoxyacrylonitrile.

Incidentally, the alcohol may be directly added to the reaction system, but an alcohol which is simultaneously formed at the time of generating nitrosyl halide in the system as mentioned below may be utilized.

As the nitrosyl halide to be used in the reaction of the present invention, there may be mentioned nitrosyl fluoride, nitrosyl chloride, nitrosyl bromide and nitrosyl iodide, and nitrosyl chloride is preferably used.

As the above-mentioned nitrosyl halide, commercially available products may be used as such, but, a nitrosyl halide may be formed and used by, for example, (1) a method in which an alkyl nitrite and a hydrogen halide are reacted (a nitrosyl halide and an alkyl alcohol are formed), or (2) a method in which an alkali metal nitrite and a hydrogen halide are reacted (a nitrosyl halide and an alkali metal halogenated salt are formed) and the like.

Incidentally, as a supplying method of the nitrosyl halide to the reaction system, commercially available products or the separately generated nitrosyl halide by the above-mentioned method (1) or (2) may be supplied, and the reaction of the above-mentioned method (1) or (2) may be directly carried out in the reaction system and the generated nitrosyl halide may be used (at that case, alkyl alcohol (in the case of (1)) or an alkali metal halogenated salt (in the case of (2)) is generated in the reaction system.). Also, the nitrosyl halide may be diluted with a gas inactive to the reaction.

An amount of the above-mentioned nitrosyl halide to be used is preferably 0.5 to 10 mols, more preferably 0.8 to 5 mols based on 1 mol of the 3-alkoxyacrylonitrile.

The reaction of the present invention is carried out in the presence or absence of a solvent. When the solvent is used, it is not specifically limited so long as it does not inhibit the reaction, and there may be mentioned, for example, alcohols such as methanol, ethanol, n-propyl alcohol, isopropyl alcohol, n-butyl alcohol, t-butyl alcohol, etc.; nitrites such as acetonitrile, propionitrile, etc.; ethers such as diethyl ether, tetrahydrofuran, dioxane, etc.; halogenated aliphatic hydrocarbons such as methylene chloride, chloroform, carbon tetrachloride, etc.; aromatic hydrocarbons such as benzene, toluene, etc.; halogenated aromatic hydrocarbons such as chlorobenzene, etc.; carboxylic acids such as acetic acid, propionic acid, etc., and an alcohol is preferably used.

An amount of the above-mentioned solvent to be used is optionally adjusted depending on uniformity or stirrability of the reaction mixture, and it is preferably 0 to 100 g, more preferably 0 to 50 g based on 1 g of the alkoxyacrylonitrile.

The reaction of the present invention can be carried out by a method in which, for example, the 3-alkoxyacrylonitrile and an alcohol are mixed and a nitrosyl halide is supplied thereto to effect the reaction, and the like. A reaction temperature at that time is preferably −70 to 50° C., more preferably −30 to 40° C., and a reaction pressure is not particularly limited.

The 3,3-dialkoxy-2-hydroxyiminopropionitrile obtained by the reaction of the present invention can be isolated and purified after completion of the reaction by a general means such as crystallization, recrystallization, distillation, column chromatography and the like.

Incidentally, in the present invention, the resulting 3,3-dialkoxy-2-hydroxyiminopropionitrile is reacted with the hydrazine compound represented by the formula (3) without isolation to produce the 5-amino-4-nitrosopyrazole compound represented by the formula (4).

The hydrazine compound to be used in the reaction of the present invention is represented by the above-mentioned formula (3). In the formula (3), $R^4$ represents a hydrogen atom, an alkyl group which may have a substituent(s) or an aryl group which may have a substituent(s). As the above-mentioned alkyl group, there may be mentioned, for example, a methyl group, an ethyl group, a propyl group, a butyl group, a pentyl group, a hexyl group and a heptyl group, etc., and as the above-mentioned aryl group, there may be mentioned, for example, a phenyl group, a naphthyl group, a pyridyl group, a pyrimidyl group, a pyrazyl group, a pyridazyl group, a quinolyl group, etc. Incidentally, these groups may include various kinds of isomers. Also, as the above-mentioned substituent(s), there may be mentioned, for example, a hydroxyl group; an alkyl group such as a methyl group, an ethyl group, a propyl group, a butyl group, etc. (these groups may include various kinds of isomers.); an alkoxy group such as a methoxy group, an ethoxy group, a propoxy group, a butoxy group, etc. (these groups may include various kinds of isomers.); an aryl group such as a phenyl group, a thienyl group, a furyl group, a pyridyl group, a pyrimidyl group, etc.; a halogen atom such as a fluorine atom, a chlorine atom, a bromine atom, an iodine atom, etc.; and a nitro group. Incidentally, the position or a number of the substituent(s) is not specifically limited. In the present invention, as the preferred alkyl group or aryl group of $R^4$, there may be mentioned, for example, a methyl group, an ethyl group, a propyl group, an isopropyl group, a n-butyl group, a t-butyl group, a phenyl group, etc., as the preferred substituted alkyl group or aryl group, there may be mentioned, for example, a 2-hydroxyethyl group, a 2-hydroxypropyl group, a benzyl group, a 2-chlorobenzyl group, a 4-chlorobenzyl group, a 4-methylphenyl group, a 4-methoxyphenyl group, a 2-chlorophenyl group, a 3-chlorophenyl group, a 4-chlorophenyl group, a 2,6-dichloro-4-trifluoromethylphenyl group, a 3-chloro-5-trifluoromethylpyridin-2-yl group, etc., as the further preferred alkyl group or aryl group, there may be mentioned, for example, a methyl group, an ethyl group, a t-butyl group, a phenyl group, etc., and as the further preferred substituted alkyl group or aryl group, there may be mentioned, for example, a 2-hydroxyethyl group, a benzyl group, a 4-methylphenyl group, a 4-methoxyphenyl group, a 4-chlorophenyl group, etc.

An amount of the above-mentioned hydrazine compound to be used is preferably 0.5 to 2.0 mol, more preferably 0.7 to 1.5 mol based on 1 mol of the 3,3-dialkoxy-2-hydroxyiminopropionitrile.

As the acid to be used in the reaction of the present invention, there may be mentioned, for example, a mineral acid such as hydrochloric acid, sulfuric acid, nitric acid, phosphoric acid, hydrobromic acid, hydroiodic acid, etc.; an organic carboxylic acid such as acetic acid, propionic acid, etc.; and an organic sulfonic acid such as methanesulfonic acid, benzenesulfonic acid, etc., preferably a mineral acid, more preferably hydrochloric acid or sulfuric acid is used. Incidentally, these acids may be used singly or in admixture of two or more kinds. In the present invention, an acid salt of the 5-amino-4-nitrosopyrazole compound corresponding to the acid to be used can be obtained.

An amount of the above-mentioned acid to be used is preferably 0.1 to 20 mol, more preferably 0.8 to 5 mol based on 1 mol of 3,3-dialkoxy-2-hydroxyiminopropionitrile.

The reaction of the present invention is carried out in the presence or absence of a solvent. When the solvent is used, it is not specifically limited so long as it does not inhibit the reaction, and there may be mentioned, for example, water; an alcohol such as methanol, ethanol, n-propyl alcohol, isopropyl alcohol, n-butyl alcohol, t-butyl alcohol, etc.; an ether such as diethyl ether, tetrahydrofuran, dioxane, etc.; an amide such as N,N-dimethylformamide, etc.; a sulfoxide such as dimethylsulfoxide, etc.; an aliphatic hydrocarbon such as pentane, hexane, heptane, cyclohexane, etc.; an aromatic hydrocarbon such as benzene, toluene, xylene, etc.; a halogenated hydrocarbon such as methylene chloride, chloroform, 1,2-dichloroethane, etc.; a nitrile such as acetonitrile, propionitrile, etc.; a carboxylic acid such as acetic acid, propionic acid, etc.; an ester such as ethyl acetate, butyl acetate, ethyl propionate, etc., preferably water; an alcohol, more preferably water; methanol, ethanol and/or isopropyl alcohol is used. Incidentally, these solvents may be used alone or in admixture of two or more kinds.

An amount of the above-mentioned solvent to be used may be optionally controlled depending on the uniformity or stirrability of the reaction solution, and it is preferably 0 to 100 g, more preferably 0 to 50 g, particularly preferably 0 to 30 g based on 1 g of 3,3-dialkoxy-2-hydroxyiminopropionitrile.

The reaction of the present invention can be carried out, for example, by mixing an acid, 3,3-dialkoxy-2-hydroxyiminopropionitrile, a hydrazine compound and a solvent, and stirring the mixture, etc. The reaction temperature at that time is preferably −20 to 150° C., more preferably 0 to 90° C., and a reaction pressure is not specifically limited.

The reaction in the other embodiment of the present invention is carried out, for example, by mixing 3,3-dialkoxy-2-hydroxyiminopropionitrile and an alcohol, supplying a nitrosyl halide, reacting preferably at −70 to 70° C., more preferably −30 to 40° C. under stirring, then, adding an acid, a hydrazine compound and a solvent to the mixture, and reacting them preferably at −20 to 150° C., more preferably 0 to 90° C. under stirring, etc. A reaction pressure at that time is not specifically limited.

An acid salt of the 5-amino-4-nitrosopyrazole compound can be obtained by the reaction of the present invention, and the resulting compound is neutralized by a base (for example, aqueous ammonia) to obtain a 5-amino-4-nitrosopyrazole compound in a free form. Incidentally, 5-amino-4-nitrosopyrazole compound or an acid salt thereof can be isolated and/or purified by an usual method such as crystallization, recrystallization, condensation, column chromatography, etc.

EXAMPLE

Next, the present invention will be explained specifically by referring to Examples, but the scope of the present invention is not limited by these Examples.

Example 1

Synthesis of
3,3-dimethoxy-2-hydroxyiminopropionitrile

To a flask having an inner volume of 300 ml and equipped with a stirring device, a thermometer, a condenser and a gas inlet tube were charged 42.83 g (0.5 mol) of 3-methoxyacrylonitrile with a purity of 97% by weight and 125 ml of methanol, and the mixture was cooled to −10° C. under stirring. Then, the reaction solution was maintained to −10 to 0° C., and while feeding nitrosyl chloride generated by reacting 170.5 g (1.0 mol) of 41% by weight aqueous sodium nitrite solution and 320 ml (3.5 mol) of conc. hydrochloric acid (the above-mentioned method (2)) in a separate apparatus to the reaction solution, the resulting mixture was reacted at −10 to 0° C. for 3 hours and at room temperature for 2 hours. After completion of the reaction, the reaction mixture was concentrated under reduced pressure, the concentrate was washed in the order of n-hexane and toluene, dried under reduced pressure at 40° C. to obtain 61.6 g of 3,3-dimethoxy-2-hydroxyiminopropionitrile (Isolation yield: 80.1%) as a pale yellowish solid with a purity of 93.7% by weight (absolute calibration curve method by high performance liquid chromatography).

The 3,3-dimethoxy-2-hydroxyiminopropionitrile is a novel compound having the following physical properties.

Melting point; 113 to 116° C. EI-MS (m/z); 113, 75, 54 CI-MS (m/z); 145 (MH$^+$)
$^1$H-NMR (CDCl$_3$, δ (ppm)); 3.46 (6H, s), 4.97 (1H, s), 8.82 (1H, brs) IR (KBr method, cm$^{-1}$); 3242, 3215, 2234, 1450, 1038, 933, 798 Elemental analysis; Carbon: 41.40%, Hydrogen: 5.53%, Nitrogen: 19.44%

(Theoretical value (C$_5$H$_8$N$_2$O$_3$); Carbon: 41.67%, Hydrogen: 5.59%, Nitrogen: 19.44%)

Example 2

Syntheses of 3,3-di-n-butoxy-2-hydroxyiminopropionitrile, 3-n-butoxy-2-hydroxyimino-3-methoxypropionitrile and 3,3-dimethoxy-2-hydroxyiminopropionitrile At room temperature, 5.0 g (60 mmol) of 3-methoxyacrylonitrile, 6.5 g (60 mmol) of n-butyl nitrite and 30 ml of diethyl ether were mixed. Then, 5 ml of the above-mentioned solution was added to a flask having an inner volume of 25 ml and equipped with a stirring device. Under stirring, 1 ml (6 mmol) of a 25.7% by weight hydrogen chloride methanol solution was gradually added dropwise, to generate nitrosyl halide and n-butyl alcohol in the reaction system (the method of the above-mentioned (1)), and the mixture was reacted at room temperature for one hour. After completion of the reaction, the reaction mixture was concentrated under reduced pressure, and after adding water to the concentrate, the mixture was extracted with toluene. The organic layer was taken out, washed with a saturated aqueous sodium hydrogen carbonate solution, and dried over anhydrous magnesium sulfate. After filtration, the filtrate was concentrated under reduced pressure, the concentrate was purified by silica gel column chromatography (Filler; Wako gel C-200 (available from Wako Junyaku Co.), Eluent; toluene/ethyl acetate=10/1 (volume ratio)) to obtain 0.06 g (Isolation yield: 4%) of 3,3-di-n-butoxy-2-hydroxyiminopropionitrile as colorless oily product, 0.21 g (Isolation yield: 19%) of 3-n-butoxy-2-hydroxyimino-3-methoxypropionitrile as colorless oily product and 0.14 g of 3,3-dimethoxy-2-hydroxyiminopropionitrile (Isolation yield: 16%) as white solid.

The 3,3-di-n-butoxy-2-hydroxyiminopropionitrile and 3-n-butoxy-2-hydroxyimino-3-methoxypropionitrile are novel compounds having the following physical properties.

Physical Properties of 3,3-di-n-butoxy-2-hydroxyiminopropionitrile

CI-MS (m/z); 229 (MH$^+$), 200, 155, 126 $^1$H-NMR (CDCl$_3$, δ (ppm)); 0.93 (6H, t), 1.34 to 1.66 (8H, m), 3.50 to 3.71 (4H, m), 6.47 (1H, s), 8.55 (1H, s)

Physical Properties of 3-n-butoxy-2-hydroxyimino-3-methoxypropionitrile

CI-MS (m/z); 187 (MH$^+$), 155, 113, 84 $^1$H-NMR (CDCl$_3$, δ ppm)); 0.94 (3H, t), 1.35 to 1.68 (4H, m), 3.46 (3H, s), 3.51 to 3.72 (2H, m), 5.02 (1H, s), 9.14 (1H, s)

Example 3

Synthesis of
3,3-dimethoxy-2-hydroxyiminopropionitrile

To a flask having an inner volume of 100 ml and equipped with a stirring device and a dropping funnel were charged 3.0 g (36 mmol) of 3-methoxyacrylonitrile, 9.0 g (63 mmol) of a 25.7% by weight hydrogen chloride methanol solution and 15 ml of methanol. Under stirring, 4.7 g (43 mmol) of n-butyl nitrite was gradually added dropwise to the mixture to generate nitrosyl halide and n-butyl alcohol in the system (the method of the above-mentioned (1)), and the mixture was reacted at room temperature for 26 hours. After completion of the reaction, a saturated sodium hydrogen carbonate was added to the mixture to neutralize the mixture, and methanol was removed from the reaction mixture by distillation under reduced pressure. The aqueous layer was extracted with ethyl acetate, the organic layer was taken out, washed with a saturated saline solution, and dried over anhydrous magnesium sulfate. After filtration, the filtrate was concentrated under reduced pressure, the concentrate was recrystallized from toluene to obtain 2.6 g of 3,3-dimethoxy-2-hydroxyiminopropionitrile (Isolation yield: 50%) as white solid.

Example 4

Synthesis of
5-amino-1-(2-hydroxyethyl)-4-nitrosopyrazole
Hydrochloride

To a flask having an inner volume of 100 ml and equipped with a stirring device, a thermometer and a reflux condenser were charged 8.43 g (55 mmol) of 3,3-dimethoxy-2-hydroxyiminopropionitrile with a purity of 94.0% by weight synthesized in the same manner as in Example 1, 4.01 g (50 mmol) of 2-hydroxyethylhydrazine with a purity of 95% by weight, 50 ml of ethanol and 7.60 g (75 mmol) of conc. hydrochloric acid, and the mixture was reacted under reflux (76 to 79° C.) for one hour. After completion of the reaction, the reaction mixture was concentrated under reduced pressure, 20 ml of toluene and 20 ml of isopropyl alcohol were added to the concentrate, and the mixture was stirred at room temperature for one hour. Then, the solution was filtered and the filtrate was dried at 40° C. under reduced pressure to obtain 6.85 g of 5-amino-1-(2-hydroxyethyl)-4-nitrosopyrazole hydrochloride (Isolation yield: 67.4%) as yellow solid with a purity of 94.8% by weight (absolute calibration curve method by high performance liquid chromatography).

Incidentally, physical properties of the 5-amino-1-(2-hydroxyethyl)-4-nitrosopyrazole hydrochloride are as mentioned below.

Melting point; 164.8 to 166.6° C. (decomposed) $^1$H-NMR (DMSO-d$_6$, δ (ppm)); 3.65 to 4.13 (4H, m), 6.80 to 10.40 (5H, m) IR (KBr method, cm$^1$); 3290, 3063, 2635, 1670, 1623, 1208, 1099, 1063, 1002, 716

Example 5

Synthesis of
5-amino-1-(2-hydroxyethyl)-4-nitrosopyrazole
Hydrochloride

To a flask having an inner volume of 25 ml and equipped with a stirring device, a thermometer and a reflux condenser were charged 1.47 g (10.0 mmol) of 3,3-dimethoxy-2-hydroxyiminopropionitrile with a purity of 98.1% by weight synthesized in the same manner as in Example 1, 0.84 g (10.5 mmol) of 2-hydroxyethylhydrazine with a purity of 95% by weight, 10 ml of methanol and 1.5 ml (18.0 mmol) of conc. hydrochloric acid, and the mixture was reacted under reflux (67° C.) for 1.5 hours. After completion of the reaction, when the reaction mixture was analyzed by high performance liquid chromatography (absolute calibration curve method), it was found that 1.81 g of 5-amino-1-(2-hydroxyethyl)-4-nitrosopyrazole hydrochloride (Reaction yield: 93.8%) had been formed.

Example 6

Synthesis of
5-amino-1-(2-hydroxyethyl)-4-nitrosopyrazole
hydrogensulfate

To a flask having an inner volume of 25 ml and equipped with a stirring device, a thermometer and a reflux condenser were charged 1.47 g (10.0 mmol) of 3,3-dimethoxy-2-hydroxyiminopropionitrile with a purity of 98.1% by weight synthesized in the same manner as in Example 1, 0.84 g (10.5 mmol) of 2-hydroxyethylhydrazine with a purity of 95% by weight, 0.54 ml of water, 10 ml of methanol and 1.18 g (12.0 mmol) of conc. sulfuric acid, and the mixture was reacted under reflux (66 to 67° C.) for 3 hours. After completion of the reaction, when the reaction mixture was analyzed by high performance liquid chromatography (absolute calibration curve method), it was found that 2.24 g of 5-amino-1-(2-hydroxyethyl)-4-nitrosopyrazole hydrogen sulfate (Reaction yield: 88.2%) had been formed.

Example 7

Synthesis of
5-amino-1-(2-hydroxyethyl)-4-nitrosopyrazole
Hydrochloride

To a flask having an inner volume of 200 ml and equipped with a stirring device, a thermometer and a reflux condenser were charged 16.86 g (110 mmol) of 3,3-dimethoxy-2-hydroxyiminopropionitrile with a purity of 94.0% by weight synthesized in the same manner as in Example. 1, 8.02 g (100 mmol) of 2-hydroxyethylhydrazine with a purity of 95% by weight, 100 ml of ethanol and 10 ml (120 mmol) of conc. hydrochloric acid, and the mixture was reacted under reflux (76 to 77° C.) for one hour. After completion of the reaction, when the reaction mixture was analyzed by high performance liquid chromatography (absolute calibration curve method), it was found that 17.62 g of 5-amino-1-(2-hydroxyethyl)-4-nitrosopyrazole hydrochloride (Reaction yield: 91.5%) had been formed.

Example 8

Synthesis of
5-amino-1-(2-hydroxyethyl)-4-nitrosopyrazole
Hydrochloride

To a flask having an inner volume of 25 ml and equipped with a stirring device, a thermometer and a reflux condenser were charged 3.37 g (22 mmol) of 3,3-dimethoxy-2-hydroxyiminopropionitrile with a purity of 94.0% by weight synthesized in the same manner as in Example 1, 1.60 g (20 mmol) of 2-hydroxyethylhydrazine with a purity of 95% by weight, 9.6 ml of isopropyl alcohol and 2 ml (24 mmol) of conc. hydrochloric acid, and the mixture was reacted under reflux (79 to 80° C.) for one hour. After completion of the reaction, when the reaction mixture was analyzed by high performance liquid chromatography (absolute calibration curve method), it was found that 3.35 g of 5-amino-1-(2-hydroxyethyl)-4-nitrosopyrazole hydrochloride (Reaction yield: 86.9%) had been formed.

Example 9

Synthesis of
5-amino-1-(2-hydroxyethyl)-4-nitrosopyrazole

To a flask having an inner volume of 25 ml and equipped with a stirring device and a thermometer were charged 2.10 g (10 mmol) of 5-amino-1-(2-hydroxyethyl)-4-nitrosopyrazole hydrochloride with a purity of 91.6% by weight synthesized in the same manner as in Example 4, 3.5 ml of water and 0.5 ml of isopropyl alcohol. Then, 1 ml (16 mmol) of 28% aqueous ammonia was gradually added dropwise to the mixture, and the resulting mixture was reacted for 30 minutes while maintaining the liquid temperature to 5° C. or lower. After completion of the reaction, precipitated crystals were collected by filtration. Then, the crystals were washed with 1 ml of cold water and 1 ml of cold isopropyl alcohol, and then dried at 40° C. under reduced pressure to obtain 1.13 g of 5-amino-1-(2-hydroxyethyl)-4-nitrosopyrazole (Isolation yield: 72.0%) as reddish orange crystal with a purity of 99.7% by weight (absolute calibration curve method by high performance liquid chromatography).

Incidentally, physical properties of the 5-amino-1-(2-hydroxyethyl)-4-nitrosopyrazole are as mentioned below.

Melting point; 170.2 to 171.8° C. (decomposed) $^1$H-NMR (DMSO-$d_6$, δ (ppm)); 3.60 to 4.03 (4H, m), 4.75 to 5.03 (1H, br), 7.06 (0.2H, s), 7.76 to 8.29 (2H, br), 8.53 (0.8H, s) IR (KBr method, cm$^{-1}$); 3346, 3168, 2960, 1658, 1529, 1497, 1243, 1072, 1016, 913, 624

Example 10

Synthesis of
5-amino-1-(2-hydroxyethyl)-4-nitrosopyrazole

To a flask having an inner volume of 50 ml and equipped with a stirring device, a thermometer and a reflux condenser were charged 4.59 g (30 mmol) of 3,3-dimethoxy-2-hydroxyiminopropionitrile with a purity of 94.3% by weight synthesized in the same manner as in Example 1, 2.98 g (31.5 mmol) of 2-hydroxyethylhydrazine with a purity of 80.5% by weight, 7.8 ml of methanol and 4.5 ml (54 mmol) of conc. hydrochloric acid, and the mixture was reacted at 50 to 52° C. for 3 hours. After completion of the reaction, 7 ml of water was added to the mixture and the resulting mixture was cooled up to 10° C. Then, 3.5 ml (58 mmol) of 28% by weight aqueous ammonia was gradually added dropwise to the mixture, and the mixture was stirred for 30 minutes while maintaining the liquid temperature to 5° C. or lower. The precipitated crystals were collected by filtration, and then, the crystals were washed with 2.5 ml of cold water and 2.5 ml of cold methanol, and dried under reduced pressure to obtain 3.40 g of 5-amino-1-(2-hydroxyethyl)-4-nitrosopyrazole (Isolation yield: 69.7%) as reddish orange crystals with a purity of 96.0% by weight (absolute calibration curve method by high performance liquid chromatography).

Example 11

Synthesis of 5-amino-1-methyl-4-nitrosopyrazole

To a flask having an inner volume of 25 ml and equipped with a stirring device, a thermometer and a reflux condenser were charged 2.97 g (20 mmol) of 3,3-dimethoxy-2-hydroxyiminopropionitrile with a purity of 96.9% by weight, 1.01 g (21 mmol) of methylhydrazine with a purity of 97% by weight, 6 ml of methanol and 3.0 ml (36 mmol) of conc. hydrochloric acid, and the mixture was reacted at 50 to 52° C. for 4 hours. After completion of the reaction, 5 ml of water was added to the mixture to cool the mixture up to 10° C., and 2.3 ml (37.9 mmol) of 28% by weight aqueous ammonia was gradually added dropwise to the mixture, and the resulting mixture was stirred for 30 minutes while maintaining the liquid temperature to 5° C. or lower. Precipitated crystals were collected by filtration, and then, the crystals were washed with 1.2 ml of cold water and 1.2 ml of cold methanol, and dried under reduced pressure to obtain 1.91 g of 5-amino-1-methyl-4-nitrosopyrazole (Isolation yield: 74.8%) as dark purple solid with a purity of 98.8% by weight (absolute calibration curve method by high performance liquid chromatography).

Incidentally, physical properties of the 5-amino-1-methyl-4-nitrosopyrazole are as mentioned below.

$^1$H-NMR (DMSO-$d_6$, δ (ppm)); 3.51 (2.4H, s), 3.58 (0.6H, s), 7.02 (0.2H, s), 7.85 to 8.20 (2H, br), 8.51 (0.8H, s) IR (KBr method, cm$^{-1}$); 3369, 3173, 1648, 1524, 1424, 1296, 1187, 1007, 937, 830, 562

Example 12

Synthesis of 5-amino-1-t-butyl-4-nitrosopyrazole

To a flask having an inner volume of 25 ml and equipped with a stirring device, a thermometer and a reflux condenser were charged, 2.97 g (20 mmol) of 3,3-dimethoxy-2-hydroxyiminopropionitrile with a purity of 96.9% by weight synthesized in the same manner as in Example 1, 2.70 g (21 mmol) of t-butylhydrazine hydrochloride with a purity of 97% by weight, 1.4 ml of water, 6 ml of methanol and 1.3 ml (15 mmol) of conc. hydrochloric acid, and the mixture was reacted at 60 to 62° C. for 3 hours. After completion of the reaction, 5 ml of water was added to the mixture and the mixture was cooled up to 10° C. Then, 2.3 ml (37.9 mmol) of 28% by weight aqueous ammonia was gradually added dropwise to the mixture, and the resulting mixture was stirred for 30 minutes while maintaining the liquid temperature to 5° C. or lower. Precipitated crystals were collected by filtration, and then, the crystals were washed with 1.2 ml of cold water and 1.2 ml of cold methanol, and dried under reduced pressure to obtain 1.93 g of 5-amino-1-t-butyl-4-nitrosopyrazole (Isolation yield: 55.2%) as reddish orange solid with a purity of 96.2% by weight (absolute calibration curve method by high performance liquid chromatography).

Incidentally, physical properties of the 5-amino-1-t-butyl-4-nitrosopyrazole are as mentioned below.

$^1$H-NMR (DMSO-$d_6$, δ (ppm)); 1.53 (7.2H, s), 1.58 (1.8H, s), 6.99 (0.2H, s), 7.80 to 8.30 (2H, br), 8.48 (0.8H, s) IR (KBr method, cm$^{-1}$); 3345, 3160, 2983, 1632, 1524, 1478, 1238, 1079, 835, 607

Example 13

Synthesis of 5-amino-1-benzyl-4-nitrosopyrazole

To a flask having an inner volume of 25 ml and equipped with a stirring device, a thermometer and a reflux condenser were charged, 2.97 g (20 mmol) of 3,3-dimethoxy-2-hydroxyiminopropionitrile with a purity of 96.9% by weight synthesized in the same manner as in Example 1, 3.43 g (21 mmol) of benzylhydrazine hydrochloride with a purity of 97% by weight, 1.4 ml of water, 6 ml of methanol and 1.3 ml (15 mmol) of conc. hydrochloric acid, and the mixture was reacted at 50 to 52° C. for 3 hours. After completion of the reaction, 5 ml of water was added to the mixture to cool the mixture up to 10° C. Then, 2.3 ml (37.9 mmol) of 28% by weight aqueous ammonia was gradually added dropwise to the mixture, and the resulting mixture was stirred for 30 minutes while maintaining the liquid temperature to 5° C. or lower. Precipitated crystals were collected by filtration, and then, the crystals were washed with 5 ml of cold water and dried under reduced pressure to obtain 3.89 g of 5-amino-1-benzyl-4-nitrosopyrazole (Isolation yield: 82.8%) as brown solid with a purity of 86.1% by weight (absolute calibration curve method by high performance liquid chromatography).

Incidentally, physical properties of the 5-amino-1-benzyl-4-nitrosopyrazole are as mentioned below.

$^1$H-NMR (DMSO-$d_6$, δ (ppm)); 5.16 (1.5H, s), 5.23 (0.5H, s), 7.04 to 7.53 (5.25H, m), 8.15 to 8.50 (2H, br), 8.59 (0.75H, s) IR (KBr method, cm$^{-1}$); 3354, 3160, 3033, 1647, 1523, 1488, 1453, 1254, 1219, 1055, 957, 836, 699

Example 14

Synthesis of 5-amino-4-nitroso-1-phenylpyrazole

To a flask having an inner volume of 25 ml and equipped with a stirring device, a thermometer and a reflux condenser were charged, 2.97 g (20 mmol) of 3,3-dimethoxy-2-hydroxyiminopropionitrile with a purity of 96.9% by weight synthesized in the same manner as in Example 1, 2.32 g (21 mmol) of phenylhydrazine with a purity of 98% by weight, 10 ml of methanol and 3.0 ml (36 mmol) of conc. hydrochloric acid, and the mixture was reacted at 50 to 52° C. for one hour. After completion of the reaction, 10 ml of water was added to the mixture to cool the same up to 10° C., then, 2.3 ml (37.9 mmol) of 28% by weight aqueous ammonia was gradually added dropwise to the mixture, and the resulting mixture was stirred for 30 minutes while maintaining the liquid temperature to 5° C. or lower for 30 minutes. Precipitated crystals were collected by filtration, and the crystals were washed with 5 ml of cold water and dried under reduced pressure to obtain 3.19 g of 5-amino-4-nitroso-1-phenylpyrazole (Isolation yield: 63.4%) as an ocherous solid with a purity of 74.9% by weight (absolute calibration curve method by high performance liquid chromatography).

Incidentally, physical properties of the 5-amino-4-nitroso-1-phenylpyrazole are as mentioned below.

$^1$H-NMR (DMSO-$d_6$, δ (ppm)); 6.83 to 7.31 (5H, m), 7.69 (0.5H, d), 8.00 (0.5H, d), 11.00 (0.5H, s), 11.29 (0.5H, s), 12.80 to 13.75 (1H, br) IR (KBr method, cm$^{-1}$); 3279, 2255, 1605, 1559, 1495, 1262, 1170, 1002, 876, 754, 689, 621, 504

Example 15

Synthesis of 5-amino-1-(4-methylphenyl)-4-nitrosopyrazole

To a flask having an inner volume of 25 ml and equipped with a stirring device, a thermometer and a reflux condenser were charged, 2.97 g (20 mmol) of 3,3-dimethoxy-2-hydroxyiminopropionitrile with a purity of 96.9% by weight synthesized in the same manner as in Example 1, 3.40 g (21 mmol) of 4-methylphenylhydrazine hydrochloride with a purity of 98% by weight, 1.4 ml of water, 10 ml of methanol and 1.3 ml (15 mmol) of conc. hydrochloric acid, and the mixture was reacted at 50 to 52° C. for one hour. After completion of the reaction, 15 ml of water and 5 ml of methanol were added to the mixture to cool the same up to 10° C., and 2.3 ml (37.9 mmol) of 28% by weight aqueous ammonia was gradually added dropwise to the mixture, and the resulting mixture was stirred for 30 minutes while maintaining the liquid temperature to 5° C. or lower. Precipitated crystals were collected by filtration, and then, the crystals were washed with 15 ml of cold water and dried under reduced pressure to obtain 3.26 g of 5-amino-1-(4-methylphenyl)-4-nitrosopyrazole (Isolation yield: 67.3%) as a yellowish solid with a purity of 83.5% by weight (absolute calibration curve method by high performance liquid chromatography).

Incidentally, physical properties of the 5-amino-1-(4-methylphenyl)-4-nitrosopyrazole are as mentioned below.

$^1$H-NMR (DMSO-$d_6$, δ (ppm)); 2.22 (1.35H, s), 2.24 (1.65H, s), 6.93 to 7.13 (4H, m), 7.66 (0.45H, s), 7.96 (0.55H, d), 10.91 (0.45H, s), 11.22 (0.55H, s), 12.70 to 13.70 (1H, br) IR (KBr method, cm$^{-1}$); 3281, 3255, 2258, 1616, 1550, 1507, 1258, 1177, 1025, 872, 811, 506

Example 16

Synthesis of 5-amino-1-(4-chlorophenyl)-4-nitrosopyrazole

To a flask having an inner volume of 25 ml and equipped with a stirring device, a thermometer and a reflux condenser were charged 2.97 g (20 mmol) of 3,3-dimethoxy-2-hydroxyiminopropionitrile with a purity of 96.9% by weight synthesized in the same manner as in Example 1, 3.96 g (21 mmol) of 4-chlorophenylhydrazine hydrochloride with a purity of 95% by weight, 1.4 ml of water, 10 ml of methanol and 1.3 ml (15 mmol) of conc. hydrochloric acid, and the mixture was reacted at 50 to 52° C. for 2 hours. After completion of the reaction, 25 ml of water and 5 ml of methanol were added to the mixture to cool the same up to 10° C., and 2.3 ml (37.9 mmol) of 28% by weight aqueous ammonia was gradually added dropwise to the mixture and the resulting mixture was stirred for 30 minutes while maintaining the liquid temperature to 5° C. or lower. Precipitated crystals were collected by filtration, and then, the crystals were washed with 10 ml of cold water and dried under reduced pressure to obtain 3.73 g of 5-amino-1-(4-chlorophenyl)-4-nitrosopyrazole (Isolation yield: 74.3%) as a yellowish solid with a purity of 88.7% by weight (absolute calibration curve method by high performance liquid chromatography).

Incidentally, physical properties of the 5-amino-1-(4-chlorophenyl)-4-nitrosopyrazole are as mentioned below.

$^1$H-NMR (DMSO-$d_6$, δ (ppm)); 7.02 to 7.38 (4H, m), 7.70 (0.45H, s), 8.01 (0.55H, s), 11.10 (0.45H, s), 11.38 (0.55H, s), 12.90 to 13.80 (1H, br) IR (KBr method, cm$^{-1}$); 3267, 2254, 1604, 1550, 1489, 1255, 1171, 1090, 1007, 875, 825, 507

Example 17

Synthesis of 5-amino-1-(4-methoxyphenyl)-4-nitrosopyrazole

To a flask having an inner volume of 25 ml and equipped with a stirring device, a thermometer and a reflux condenser were charged, 2.97 g (20 mmol) of 3,3-dimethoxy-2-hydroxyiminopropionitrile with a purity of 96.9% by weight synthesized in the same manner as in Example 1, 3.74 g (21 mmol) of 4-methoxyphenylhydrazine hydrochloride with a purity of 98% by weight, 1.4 ml of water, 10 ml of methanol and 1.3 ml (15 mmol) of conc. hydrochloric acid, and the mixture was reacted at 50 to 52° C. for one hour. After completion of the reaction, 25 ml of water and 5 ml of methanol were added to the mixture to cool the same up to 10° C., and 2.3 ml (37.9 mmol) of 28% by weight aqueous ammonia was gradually added dropwise to the mixture and the resulting mixture was stirred for 30 minutes while maintaining the liquid temperature to 5° C. or lower. Precipitated crystals were collected by filtration, and then, the crystals were washed with 10 ml of cold water and dried under reduced pressure to obtain 3.07 g of 5-amino-1-(4-methoxyphenyl)-4-nitrosopyrazole (Isolation yield: 55.3%) as a yellowish solid with a purity of 78.6% by weight (absolute calibration curve method by high performance liquid chromatography).

Incidentally, physical properties of 5-amino-1-(4-methoxyphenyl)-4-nitrosopyrazole are as mentioned below.

$^1$H-NMR (DMSO-$d_6$, δ (ppm)); 3.70 (1.35H, s), 3.71 (1.65H, s), 6.86 to 7.07 (4H, m), 7.63 (0.45H, d), 7.93 (0.55H, d), 10.87 (0.45H, s), 11.19 (0.55H, s), 12.70 to 13.50 (1H, br) IR (KBr method, cm$^{-1}$); 3305, 3013, 2264, 1552, 1515, 1465, 1227, 1174, 1008, 832, 571, 525

Example 18

Synthesis of 5-amino-1-(2-hydroxyethyl)-4-nitrosopyrazole

To a flask having an inner volume of 500 ml and equipped with a stirring device, a thermometer, a reflux condenser and a gas inlet tube were charged 42.5 g (0.50 mol) of 97.7% by weight 3-methoxyacrylonitrile and 165 ml of methanol, and the mixture was cooled up to 15° C. under stirring. Then, while maintaining the reaction solution to 15 to 25° C., nitrosyl chloride generated by reacting 171.1 g (1.0 mol) of 41% by weight aqueous sodium nitrite solution and 304.2 g (3.0 mol) of 36% by weight hydrochloric acid in a separate vessel was fed to the reaction solution over 1.5 hours, and the mixture was reacted at 15 to 20° C. for one hour under stirring.

Then, nitrogen was blown in the reaction solution to remove nitrosyl chloride, a mixed solution of 42.3 g (0.5 mol) of 80.5% by weight 2-hydroxyethylhydrazine and 60.8 g (0.60 mol) 36% by weight hydrochloric acid was gradually added to the reaction solution while maintaining the temperature thereof to 50° C., and the mixture was reacted at 50° C. for 3 hours under stirring. After completion of the reaction, 120 ml of water was added to the reaction mixture to make the liquid temperature 10° C., and 70 ml (1.12 mol) of 28% by weight aqueous ammonia was gradually added to the mixture to neutralize the same, so that crystals were precipitated. Moreover, the reaction mixture was cooled up to 5° C. and stirred for 30 minutes. Crystals were collected by filtration, washed successively with 30 ml of cold water and 30 ml of cold methanol and dried under reduced pressure to obtain 57.5 g of 5-amino-1-(2-hydroxyethyl)-4-nitrosopyrazole (Isolation yield: 69.8%) as red-orange crystals with a purity of 94.8% by weight (absolute calibration curve method by high performance liquid chromatography).

Example 19

Synthesis of 5-amino-1-(2-hydroxyethyl)-4-nitrosopyrazole)

To a flask having an inner volume of 100 ml and equipped with a stirring device, a thermometer, a gas inlet tube and a dry ice condenser (ethanol and dry ice were charged in a Dewar condenser) were charged, 10.28 g (0.12 mol) of 97.0% by weight 3-methoxyacrylonitrile and 30 ml of methanol, and the mixture was cooled up to 5° C. while stirring. Then, while maintaining the temperature of the reaction solution to 5 to 20° C., nitrosyl chloride generated by reacting 34.0 g (0.20 mol) of 41% by weight aqueous sodium nitrite solution and 60.8 g (0.60 mol) of 36% by weight hydrochloric acid in a separate vessel were fed to the reaction vessel over 40 minutes, and the mixture was reacted for 2 hours under stirring at 5 to 20° C.

Then, an inner atmosphere of the reaction vessel was replaced with nitrogen, and 7 ml of methanol and nitrosyl halide were removed under reduced pressure. To the reaction solution were gradually added 13 ml of methanol, 9.61 g (0.12 mol) of 95% by weight 2-hydroxyethylhydrazine and 14.6 g (0.14 mol) of 36% by weight hydrochloric acid in this order, and the mixture was reacted for 3 hours under stirring at 50° C. After completion of the reaction, 30 ml of water was added to the reaction mixture to cool the same to 10° C., and 15 ml (0.25 mol) of 28% by weight aqueous ammonia was gradually added to neutralize the mixture, so that crystals were precipitated. Moreover, the reaction mixture was cooled up to 5° C. and stirred for 30 minutes. Crystals were collected by filtration, washed successively with 8 ml of cold water and 8 ml of cold methanol and dried under reduced pressure to obtain 13.46 g of 5-amino-1-(2-hydroxyethyl)-4-nitrosopyrazole (Isolation yield: 70.1%) as red-orange crystals with a purity of 97.6% by weight (absolute calibration curve method by high performance liquid chromatography).

Example 20

Synthesis of 5-amino-1-(2-hydroxyethyl)-4-nitrosopyrazole

To a flask having an inner volume of 500 ml and equipped with a stirring device, a thermometer, a reflux condenser and a gas inlet tube were charged 50.0 g (0.59 mol) of 97.0% by weight 3-methoxyacrylonitrile and 177 ml of methanol, and the mixture was cooled to 15° C. under stirring. Then, while maintaining the temperature of the reaction solution to 15 to 25° C., nitrosyl chloride generated by reacting 203.4 g (1.18 mol) of 41% by weight aqueous sodium nitrite solution and 359.0 g (3.54 mol) of 36% by weight hydrochloric acid in a separate vessel were fed to the reaction solution over 1.5 hours, and the mixture was reacted for one hour under stirring at 15 to 20° C.

Then, nitrogen was blown into the reaction solution to remove nitrosyl chloride, and 18 ml of methanol was added thereto to cool the same up to 10° C. To the reaction solution was gradually added 56.1 g (0.59 mol) of 80.0% by weight 2-hydroxyethylhydrazine, and 71.8 g (0.60 mol) of 36% by weight hydrochloric acid was gradually added to the same while maintaining the solution to 50° C., and the mixture was reacted under stirring at the same temperature for 3 hours. After completion of the reaction, 150 ml of water was added to the reaction mixture to make the liquid temperature 10° C., and 87 ml (1.43 mol) of 28% by weight aqueous ammonia was gradually added to the mixture to neutralize the same, so that crystals were precipitated. Moreover, the reaction mixture was heated to 40° C. and stirred for 20 minutes, then, cooled up to 5° C. and stirred for 30 minutes. Crystals were collected by filtration, washed with 70 ml of cold water and dried under reduced pressure to obtain 63.0 g of 5-amino-1-(2-hydroxyethyl)-4-nitrosopyrazole (Isolation yield: 67.4%) as red-orange crystals with a purity of 98.6% by weight (absolute calibration curve method by high performance liquid chromatography).

UTILIZABILITY IN INDUSTRY

According to the present invention, a novel 3,3-dialkoxy-2-hydroxyiminopropionitrile which is useful as an intermediate starting material for medicine, agricultural chemical, etc., and a process for preparing the same can be provided.

Also, according to the present invention, it can be provided a process for preparing an objective 5-amino-4-nitrosopyrazole compound or an acid salt thereof with a high yield from the above-mentioned 3,3-dialkoxy-2-hydroxyiminopropionitrile which can be easily available with a simple and easy method.

The invention claimed is:

1. A 3,3-dialkoxy-2-hydroxyiminopropionitrile represented by the formula (1):

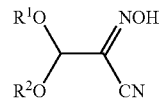

(1)

wherein $R^1$ and $R^2$ may be the same or different from each other, and each represent an alkyl group having 1 to 8 carbon atoms.

2. The 3,3-dialkoxy-2-hydroxyiminopropionitrile according to claim 1, wherein $R^1$ and $R^2$ may be the same or different from each other, and each represent a methyl group or a butyl group.

3. A process for preparing a 3,3-dialkoxy-2-hydroxyiminopropionitrile represented by the formula (1):

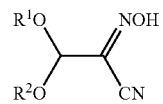

(1)

wherein $R^1$ and $R^2$ may be the same or different from each other, and each represent an alkyl group having 1 to 8 carbon atoms, which comprises reacting a 3-alkoxyacrylonitrile represented by the formula (2):

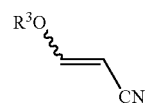

(2)

wherein $R^3$ represents an alkyl group having 1 to 4 carbon atoms, with a natrosyl halide in the presence of an alcohol.

4. The process according to claim 3, wherein the alcohol as an alcohol having an alkyl group with 1 to 8 carbon atoms.

5. The process according to claim 3, wherein the alcohol is at least one selected from the group consisting of methanol, ethanol, n-propyl alcohol, isopropyl alcohol, n-butyl alcohol, t-butyl alcohol, pentyl alcohol, hexyl alcohol, heptyl alcohol and octyl alcohol.

6. The process according to claim 3, wherein the alcohol is at least one selected from the group consisting of methanol, ethanol, n-propyl alcohol, isopropyl alcohol, n-butyl alcohol and t-butyl alcohol.

7. The process according to claim 3, wherein the alcohol is used in an amount of 0.5 to 100 mol per mol of the 3-alkoxyacrylonitrile.

8. The process according to claim 3, wherein the alcohol is used in an amount of 0.8 to 50 mol per mol of the 3-alkoxyacrylonitrile.

9. The process according to claim 3, wherein the nitrosyl halide is used in an amount of 0.5 to 10 mol per mol of the 3-alkoxyacrylonitrile.

10. The process according to claim 3, wherein the nitrosyl halide is used in an amount of 0.8 to 5 mol per mol of the 3-alkoxyacrylonitrile.

* * * * *